(12) United States Patent
Kretschmar et al.

(10) Patent No.: US 7,659,247 B2
(45) Date of Patent: *Feb. 9, 2010

(54) PRODUCTION OF A VON WILLEBRAND FACTOR PREPARATION HAVING A HIGH SPECIFIC ACTIVITY

(75) Inventors: Michael Kretschmar, Seligenstadt (DE); Wolfgang Moeller, Oberusel (DE)

(73) Assignee: Biotest AG, Dreieich (DE)

( * ) Notice: Subject to any disclaimer, the term of this patent is extended or adjusted under 35 U.S.C. 154(b) by 394 days.

This patent is subject to a terminal disclaimer.

(21) Appl. No.: 10/594,454

(22) PCT Filed: Sep. 9, 2005

(86) PCT No.: PCT/EP2005/009729

§ 371 (c)(1),
(2), (4) Date: Sep. 26, 2006

(87) PCT Pub. No.: WO2006/029774

PCT Pub. Date: Mar. 23, 2006

(65) Prior Publication Data

US 2007/0135619 A1      Jun. 14, 2007

(30) Foreign Application Priority Data

Sep. 14, 2004   (DE)   ........................ 10 2004 044 421

(51) Int. Cl.
*C07K 14/745* (2006.01)

(52) U.S. Cl. .............................. 514/12; 514/2; 530/383; 530/350

(58) Field of Classification Search ....................... 514/2, 514/12; 530/383, 350
See application file for complete search history.

(56) References Cited

U.S. PATENT DOCUMENTS 5,128,245 A      7/1992   Greenberg et al.

OTHER PUBLICATIONS

Federici, Augusto B., "The Factor VIII/von Willebrand Factor Complex: Basic and Clinical Issues", J. Hematology, vol. 88, suppl. 9, pp. 3-12 (May 2003).
Gorman, J. J. et al., "Studies on The Structure and Subunit Composition of Human Antihaemophilic Factor", Thrombosis Research, vol. 12, pp. 341-352 (1978).
Saundry, R. H. et al., "Chromatography of vWF on Dextran Sulphate Sepharose", Thrombosis Research, vol. 48, pp. 641-652 (1987).
Janson, J.C. et al. (editors), "Protein Purification: Principles, High Resolution Methods, and Applications", Second edition, Wiley-Liss, NY, pp. 190-191, 199-200 (1998).
Bernardi, Giorgio, "Chromatography of Proteins on Hydroxyapatite", Methods in Enzymology, vol. 27, pp. 471-479 (1973).
Barington, K. A. et al., "A Very High Purity Von Willebrand Factor Preparation Containing High Molecular Weight Multimers", Vox Sanguinis, vol. 76, pp. 85-89 (Mar. 1999).
Lethagen, S. et al., "A Comparative In Vitro Evaluation of Six Von Willebrand Factor Concentrates", Haemophilia, vol. 10, No. 3, pp. 243-249 (May 2004).
Burnouf-Radosevich, M. et al., "Chromatographic Preparation of a Therapeutic Highly Purified Von Willebrand Factor Concentrate from Human Cryoprecipitate", Vox Sanguinis, vol. 62, No. 1, pp. 1-11 (1992).
Veyradier, A. et al., "Laboratory Diagnosis of Von Willebrand Disease", vol. 28, No. 4, pp. 201-210 (Dec. 1998).
Written Opinion of the International Searching Authority issued in PCT/EP05/009729 (PCT/ISA/237), (Jan. 2004).

*Primary Examiner*—Chih-Min Kam
(74) *Attorney, Agent, or Firm*—Chalin Smith; Smith Patent Consulting, LLC

(57) ABSTRACT

This invention relates to a process for the production of a von Willebrand factor preparation having a high specific activity, hydroxylapatite being used as a chromatography medium.

15 Claims, No Drawings

PRODUCTION OF A VON WILLEBRAND FACTOR PREPARATION HAVING A HIGH SPECIFIC ACTIVITY

This application is a Rule 371 U.S. National Phase Filing of PCT/EP05/009729, filed Sep. 9, 2005, which, in turn, claims priority to German Patent Application No. 10 2004 044 421.8, filed Sep. 14, 2004, the contents of which are incorporated by reference herein in their entirety.

This invention relates to a process for the production of a von Willebrand factor preparation having a high specific VWF activity, hydroxylapatite being used as a chromatography medium.

The von Willebrand factor is a glycoprotein which is synthesized in endothelial cells and megakaryocytes. The molecular weight of the monomer is about 225,000 Da. Within the cell, the formation of disulfide bridges results in dimers which, in turn, associate into oligomers of up to 40 dimeric subunits, also via disulfide linkages. The concentration of the von Willebrand factor (VWF) released into the plasma is 5-10 mg/l.

In primary hemostasis, it is the object of VWF to arrange for the adhesion of thrombocytes to injured subendothelium and, under the conditions of high shear forces as in the arterial system, to support the thrombocyte aggregation. As a function in secondary hemostasis, VWF binds factor VIII, an important cofactor in blood coagulation, in a non-covalent complex. Factor VIII is thus stabilized and protected against premature degradation.

The von Willebrand syndrome (VWS) is a bleeding disorder which is caused by a quantitative or qualitative change in VWF. Plasmatic factor VIII preparations having a rather high VWF content are frequently used to treat the severe form of VWS. Although, bleedings can be staunched by this, the thrombosis risk simultaneously increases, in particular in the case of frequent or prolonged use. This is due to an overdosage of factor VIII. The therapy of ill persons suffering from VWS with highly pure, factor VIII deficient/factor VIII free VWF concentrates is much more favorable in terms of patient safety.

A frequent problem of the production of a VWF preparation is the loss of specific VWF activity. According to the above mentioned definition, the specific VWF activity is 100-200 U per mg VWF antigen with a VWF concentration of 5-10 μg/ml in the blood and a defined activity of 1 U/ml on the average. As a rule, the specific VWF activity drastically decreases during the first recovery steps for the production of VWF preparations. This loss of specific activity correlates structurally with proteolytic degradation reactions which lower the content of high-molecular VWF molecules (multimers) and raises the content of low-molecular VWF molecules (dimers/tetramers). With respect to a therapeutic preparation it is desirable to remove the less active low-molecular VWF oligomers which form during the recovery of plasma fractions. VWF solutions having a low specific VWF activity have a content of less desired low-molecular VWF oligomers higher than that of VWF solutions having a high specific VWF activity. A process would be desirable by which therapeutically active preparations having a specific activity of >100 U per mg VWF antigen can be produced from a source having a specific activity of <100 U per mg VWF antigen.

Literature has described various processes which aim at raising the specific VWF activity:

WO 98/38219 describes a process for the isolation of VWF, in which VWF is bound to a cation exchanger at a low salt concentration and VWF having a high specific activity is recovered by fractional elution.

WO 96/10584 describes a process for isolating highly pure recombinant VWF by means of combined anion exchange/heparin affinity chromatography, and EP 0 705 846 discloses the isolation of high-molecular and low-molecular fractions of recombinant VWF by means of heparin affinity chromatography.

The processes described thus far are unfavorable as regards profitability and purification efficiency. When a heparin affinity chromatography was used to increase the specific VWF activity, the activity of a previously purified protein solution containing recombinant VWF was raised from 4.3 U per mg VWF antigen to 7.3 U/mg, for example. The final specific VWF activity of the recombinant protein is low. The affinity chromatography cost is comparatively high. Better results were achieved by using a cation exchange chromatography. A purification by means of a recombinant antibody resulted in a specific VWF activity of 30.4 U/mg in combination with upstream anion exchange and immunoaffinity chromatographies. An attained purity of 65 U per mg protein was reached by purifying a plasmatic VWF by the combination of anion exchange and cation exchange chromatographies. The increase in the specific VWF activity (activity per VWF antigen amount) was not dealt with.

There is a need for an economic process with which sparsely active VWF molecules can be depleted from a protein fraction so as to raise the specific activity. In this connection, a specific VWF activity shall be obtained which corresponds to that in the plasma of healthy persons. According to the invention this object is achieved by a chromatographic separation step using hydroxylapatite.

The present invention relates to a process for separating VWF having a high specific activity from VWF having a low specific activity, comprising a chromatography with hydroxylapatite as a chromatography matrix. For example, a value of >120 U per mg VWF antigen is referred to as a high specific VWF activity and a value of <70 U per mg VWF antigen is regarded as a low specific VWF activity. Depending on the quality of the starting material, highly active fractions and/or fractions having low activity can be defined differently. A further aspect of the invention is a process for the production of a composition having a high specific VWF activity, characterized in that a VWF containing composition is purified by hydroxylapatite chromatography. The invention also relates to a process for increasing the specific VWF activity of a VWF containing composition, characterized in that the WVF containing composition is subjected to a hydroxylapatite chromatography.

Hydroxylapatite is a form of calcium phosphate having the composition $Ca_5(PO_4)_3OH$ or $Ca_{10}(PO_4)_6OH_2$ which can be used as a stationary phase for the chromatography of proteins, nucleic acids and other macromolecules. Along with the crystalline form of hydroxylapatite it is also possible to use a ceramic form which can be obtained by sintering. Hydroxylapatite can be bought from the Bio-Rad company (Munich, Germany), for example. Its ceramic hydroxylapatite is provided in two forms (type 1 and type 2). On account of larger surface areas, the type 1 material has a greater binding capacity for relatively small molecules, e.g. small proteins. In contrast, the particles of the type 2 material have larger pores which enable the penetration and thus better binding of large molecules, e.g. DNA or large proteins. These materials preferably have the following properties:

TABLE 1

| | Dynamic binding capacity | Nominal pore diameter |
|---|---|---|
| Type 1 | >13.7 mg lysozyme/ml CHT* | 600-800 Å |
| Type 2 | >6.8 mg lysozyme/ml CHT* | 800-1000 Å |

*CHT = ceramic hydroxylapatite

Crystalline or ceramic hydroxylapatite is freely available. Processes for the production thereof are known in the art. Based on the present invention, the use of ceramic hydroxylapatite is preferred.

Hydroxylapatite, in particular in its ceramic stabilized form, is extremely well suited to carry out processes on an industrial scale. On account of its separating characteristics, hydroxylapatite offers a better resolution than the frequently described ion exchange chromatography media. In the hydroxylapatite purification method, neither calcium nor amino acids have to be added to the buffers.

The process can be carried out as a column chromatography or a batch process; it is preferred to conduct a column chromatography.

The process usually comprises that
(a) VWF is bound to the hydroxylapatite matrix,
(b) VWF having a low specific VWF activity is washed out at a medium salt concentration, and
(c) VWF having a high specific VWF activity is subsequently eluted at a higher salt concentration.

In step (a), a solution containing VWF having high and low specific VWF activities is contacted with the hydroxylapatite matrix. The total concentration of sodium and/or potassium phosphate in this solution is usually 0 to 200 mM, preferably 1 to 100 mM, more preferably 1 to 50 mM, most preferably 10 to 30 mM.

In wash step (b), the hydroxylapatite matrix is washed with a buffer having a medium salt concentration. The total concentration of sodium and/or potassium phosphate in this wash buffer is usually 100 to 300 mM, preferably 200 to 300 mM, more preferably 200 to 270 mM, most preferably 210 to 250 mM. In this connection, VWF having a low specific VWF activity is washed out. The higher the pH value of the buffer, the lower the salt concentration may be chosen.

In step (c), VWF having a high specific VWF activity can be eluted with a buffer having a relatively high salt concentration. The elution buffer usually contains 200 to 500 mM, preferably 250 to 500 mM, more preferably 300 to 400 mM, sodium and/or potassium phosphate.

Yield and purity can be changed by changing the salt concentrations. The higher the salt concentration in the wash buffer, the more active the resulting fraction of interest. However, the yield is lowered by this. Furthermore, the selected pH value influences the optimum salt concentration for the wash buffer. The lower the pH, the stronger the binding of VWF to the hydroxylapatite matrix. Correspondingly, the selected salt concentrations can be higher with lower pH values and lower with higher pH values.

Hydroxylapatite chromatography is carried out at a pH of 5 to 7, preferably 5.5 to 6.8, more preferably 6.0 to 6.8, most preferably 6.2 to 6.5. Running, wash and elution buffers and the protein solution to be applied usually have the same pH. However, variants where these solutions have different pH values are also practicable.

Depending on the pH conditions and aspired yields, sparsely active VWF molecules can be eluted by hydroxylapatite columns with buffers having a medium salt concentration. At pH 6.0, for example, buffers can be used which contain 200 to 270 mM sodium or potassium phosphate, preferably 220 to 250 mM sodium phosphate. At pH 6.5, for example, buffers would be suited which contain 180 to 260 mM, preferably 210 to 250 mM, sodium or potassium phosphate. Having separated the sparsely active VWF molecules, the highly active VWF molecules can be eluted with a high salt buffer, e.g. 250 to 500 mM sodium or potassium phosphate, preferably 300 to 400 mM sodium or potassium phosphate.

The binding hydroxylapatite chromatography according to the invention can be combined with other purification techniques. It has proved particularly favorable to initially carry out "flow chromatography" with hydroxylapatite to deplete the main contaminations. Thereafter, the flow fraction is applied onto a hydroxylapatite column, as described above. VWF molecules are bound and VWF having a high specific VWF activity is eluted selectively.

In a particular embodiment, a flow chromatography with hydroxylapatite is initially carried out, VWF not binding to the hydroxylapatite matrix, and then the flow fraction is re-chromatographed under binding conditions and the VWF fraction having a high specific VWF activity is eluted.

A "flow chromatography" within the meaning of this application comprises that (i) a composition containing VWF and one or more contaminating proteins is contacted with a hydroxylapatite matrix so as to bind at least one contaminating protein to the hydroxylapatite matrix while VWF is not substantially bound to the hydroxylapatite matrix, and optionally thereafter (ii) unbound VWF is separated from the hydroxylapatite matrix. In the case of column chromatography, WVF is in the flow and at least one contaminating protein, e.g. fibronectin and/or fibrinogen, is bound to the hydroxylapatite.

The flow chromatography is carried out at a pH of 6.5 to 8.5, preferably 6.8 to 8.5, more preferably 6.8 to 7.5, most preferably 7.0 to 7.5. Running buffers, wash buffers and elution buffers and the protein solution to be applied usually have the same pH. However, variants are also practicable where these solutions have different pH values.

The VWF containing composition which, in the flow chromatography, is contacted with the hydroxylapatite matrix, preferably contains sodium phosphate and/or potassium phosphate. The total concentration of sodium phosphate and/or potassium phosphate in the solution is e.g. 0 to 100 mM, preferably 10 to 50 mM, most preferably 20 to 40 mM, i.e. a buffer solution having said concentrations can be used as a running buffer.

As a result of the preceding step of flow chromatography it is possible to obtain VWF preparations which only contain minor amounts of fibrinogen and fibronectin. The concentration of fibrinogen antigen in the flow fraction is usually below 25 μg/ml, preferably below 15 μg/ml, more preferably below 10 μg/ml, most preferably at most 5 μg/ml. The concentration of fibronectin antigen in the flow fraction is usually below 250 μg/ml, preferably below 150 μg/ml, more preferably below 100 μg/ml, most preferably at most 50 μg/ml. The concentration of fibrinogen antigen and fibronectin antigen can be determined by generally known processes.

As a result of the preceding step of flow chromatography, a considerable depletion of the contaminating proteins fibrinogen and fibronectin can be achieved. Thus, the fibrinogen concentration in the flow fraction is preferably below 10%, more preferably below 5%, even more preferably below 2.5%, of the fibrinogen concentration in the loading solution (prior to flow chromatography). The fibronectin concentration in the flow fraction is preferably below 10%, more preferably below 5%, even more preferably below 2.5%, of the fibronectin concentration in the loading solution (prior to flow chromatography).

The yield of flow chromatography (based on the mass balance) is usually above 50%, preferably above 60%, most preferably above 75%. In connection with flow chromatography it is useful, but not necessary, to use phosphate ions as a buffer substance. Phosphate is a specific agent for the elution of VWF in the binding chromatography.

In general, VWF containing solutions, in particular VWF containing plasma fractions, can be used as starting materials. VWF can be bound to a hydroxylapatite column at pH values of preferably 6.0 to 6.8, more preferably 6.2 to 6.5, at a low salt concentration of 0-100 mM, preferably 10-50 mM, potassium or sodium phosphate.

In a particular embodiment, it is possible to use fluoroapatite in place of pure hydroxylapatite as a chromatography matrix. Fluoroapatite is produced by reacting hydroxylapatite with a fluoride containing substance. The Bio-Rad company (Munich, Germany) produces e.g. ceramic fluoroapatite by a 90% conversion of ceramic hydroxylapatite with a fluorine reagent. As compared to hydroxylapatite, fluoroapatite is markedly more stable under acidic pH conditions. Therefore, fluoroapatite is usually used to carry out chromatographies at a pH lower than technically useful for hydroxylapatite. Regarding a purification of highly active VWF molecules with fluoroapatite, the chromatography can be carried out in way similar to the process proposed for hydroxylapatite. Salt concentrations have to be adapted to the selected pH value (>=5.0).

The process according to the invention can also comprise one or more of the following steps:
(1) quick-freezing at a temperature of below −30° C. and thawing near 0° C. (cryoprecipitation)
(2) ethanol precipitation or adsorption on aluminum hydroxide
(3) virus inactivation of the VWF containing composition by solvent/detergent treatment
(4) anion exchange chromatography
(5) precipitation of fibronectin by adjusting a pH to below pH 5.4
(6) affinity chromatography
(7) diafiltration or ultrafiltration
(8) rebuffering or dialysis or gel filtration
(9) sterile filtration
(10) lyophilization
(11) virus inactivation by heat treatment (e.g. about 30 min at about 100° C.)

Process steps (1) to (5) are preferably carried out prior to the hydroxylapatite chromatography. However, it is also possible to carry out less than the 5 process steps. The sequence of the steps is not compulsory.

Steps (6) to (11) can be carried out, where desired. In particular, affinity chromatography is not necessary since a high purity can already be achieved by the hydroxylapatite chromatography.

Thus, a previously purified plasma fraction can be used as a starting material for the processes of the present invention. It may be a further purified cryoprecipitate solution. For example, the cryoprecipitate solution can be precipitated with aluminum hydroxide and/or be further purified chromatographically. Thus, the cryoprecipitate solution can be precipitated with aluminum hydroxide, for example, and then be further purified by means of anion exchange chromatography. It is also preferred for the cryoprecipitate solution to be subjected to virus inactivation. A preferred process for the virus inactivation is a solvent/detergent treatment as described in U.S. Pat. No. 4,540,573.

A protein solution containing recombinant VWF (rVWF) from cell culture supernatants can also be used as a starting material. The expression "rVWF" covers both VWF having the wild-type sequence and variants having an amino acid sequence modified with respect to a wild-type VWF, wherein one or more amino acids may be substituted, deleted and/or added. The variants usually have VWF activity. Processes for the production of suitable expression vectors, for introducing the vectors into the host cells and for culturing the host cells are generally known to the person skilled in the art (Fischer et al., Structural analysis of recombinant von Willebrand factor: identification of hetero and homo-dimers.

FEBS Lett 1994; 351:345-348. Fischer et al., Structural analysis of recombinant von Willebrand factor produced at industrial scale fermentation of transformed CHO cells co-expressing recombinant furin. FEBS Left 1995; 375:259-262).

In particular, when plasma fractions are used, a pH precipitation can be carried out prior to the hydroxylapatite chromatography to separate fibronectin. The pH precipitation serving for separating fibronectin from a plasma fraction comprises e.g. that
(i) the pH value of the plasma fraction is adjusted to below pH 5.4 so as to form a precipitate, and
(ii) the precipitate formed is separated.

In this connection, the expression "plasma fraction" refers to a composition which was obtained from plasma and contains various plasma proteins. The plasma fraction which is used as a starting composition in step (i), is a liquid composition. Preferably, the liquid composition is a solution or a suspension, most preferably the composition is a solution. In a particular embodiment, the plasma fraction is dissolved cryoprecipitate. This dissolved cryoprecipitate can be previously purified by various processes. Examples are aluminum hydroxide treatment, solvent/detergent treatment and/or anion exchange chromatography. The concentration of sodium chloride or potassium chloride in the plasma fraction is preferably 50 to 250 mM, more preferably 100 to 200 mM, most preferably 120 to 150 mM. The plasma fraction may contain e.g. the following buffer substances: citrate ions, acetate ions, phosphate ions and/or amino acids.

The fibronectin concentration in the plasma fraction, which is subjected to step (i), is usually at least 0.05 g/l, preferably at least 0.1 g/l, more preferably at least 0.25 g/l, most preferably at least 0.5 g/l. The fibronectin concentration in the plasma fraction can be 0.1 to 5 g/l, preferably 0.1 to 2 g/l, for example.

In order to separate fibronectin from the plasma fraction, the pH value of the plasma fraction is adjusted below pH 5.4. In this connection, a precipitate forms which contains fibronectin. Preferably, the pH is adjusted to below pH 5.3, more preferably to below pH 5.2. The adjusted pH is thus preferably within a range of pH 4.5 to below 5.4, preferably within a range of pH 4.7 to 5.3, more preferably within a range of pH 4.8 to 5.2, even more preferably within a range of pH 4.9 to 5.1. The adjustment of the pH is usually achieved by adding an acidic component. Various acids may be used as the acidic component, e.g. hydrochloric acid, phosphoric acid or acetic acid. The acidic component is usually added over a certain period of time, e.g. drop-wise. Thus, a pH within the range defined above in more detail is gradually adjusted ("titrated").

During and after the pH adjustment, the plasma fraction is preferably kept moving or mixed, e.g. by stirring. It is also preferred that after the pH adjustment the plasma fraction is further mixed for a certain period of time (e.g. by stirring), in general for at least 10 minutes, preferably for at least 20 minutes, most preferably for a period of 30 to 90 minutes. During this period, sticky aggregates form which have a considerable fibronectin content. Therefore, according to a preferred embodiment a suitable stirrer, e.g. an anchor agitator or paddle mixer, shall be used to the agitator blade of which the precipitate adheres. Thus, the precipitated fibronectin can easily be removed from the solution.

The pH precipitation for the separation of fibronectin can be carried out within a wide temperature spectrum, e.g. from about 1° C. to about 37° C. Preferred temperature ranges are 4 to 35° C., more preferably 10 to 30° C., most preferably the process is carried out from 20 to 25° C.

The fibronectin concentration in the plasma fraction can be reduced by at least 50% by pH precipitation to separate fibronectin from plasma fractions. The fibronectin concentration in the plasma fraction is preferably reduced by 70 to 99%, more preferably by 80 to 99%, most preferably by 90 to 98% or by 95 to 98%. In a particular embodiment, the loss of VWF in the precipitation step is at most 50%, preferably at most 40%, more preferably at most 30%, even more preferably at most 20%, most preferably at most 10%.

A further aspect of the present invention is a VWF containing composition which can be obtained by a process according to the invention as described in the present application. Preferably, it is a substantially pure VWF preparation. "Substantially pure" means that the composition is substantially free of other proteins, in particular that no fibronectin and no fibrinogen can be identified.

The VWF preparation according to the invention can have a specific activity of at least 75 U/mg protein, preferably it has a specific activity of at least 85 U/mg protein, more preferably at least 100 U/mg protein, most preferably at least 120 U/mg protein. Thus, specific activities of >100 U per mg protein can be obtained by the process according to the invention. The VWF activity can be determined as described in the examples. The specific activity (U/mg protein) can be increased by at least 100%, preferably by at least 150%, most preferably by at least 175%, by means of the hydroxylapatite chromatography according to the invention.

The composition according to the invention preferably has a specific VWF activity of at least 50 U/mg VWF antigen, more preferably at least 75 U/mg VWF antigen, even more preferably at least 100 U/mg VWF antigen, even more preferably at least 120 U/mg VWF antigen, even more preferably at least 125 U/mg VWF antigen, most preferably at least 150 U/mg VWF antigen. The specific VWF activity (U/mg VWF antigen) can be raised by at least 20%, preferably by at least 35%, most preferably by at least 50%, by means of the hydroxylapatite chromatography according to the invention.

A further aspect of the invention is the use of hydroxylapatite for the production of a VWF preparation having a high specific VWF activity. The invention also relates to the use of hydroxylapatite to separate VWF having a high specific VWF activity from VWF having a low specific VWF activity. Furthermore, the invention relates to the use of hydroxylapatite to raise the specific VWF activity of a composition containing VWF. The preferred embodiments of the use according to the invention correspond to those of the process according to the invention and the composition according to the invention.

A further aspect of the invention is the use of the inventive VWF compound, VWF composition or the VWF preparation to treat the von Willebrand syndrome.

The invention also relates to the use for the production of a medicament to treat the von Willebrand syndrome.

The various embodiments described in this application may be combined.

The below examples explain the invention in more detail.

EXAMPLE 1

Increase in the Specific VWF Activity of a Previously Purified VWF Containing Plasma Fraction by Means of Hydroxylapatite Chromatography on a Laboratory Scale The VWF containing protein solution passed through the following preliminary purification steps: A cryoprecipitate solution was subjected to an aluminum hydroxide precipitation. Thereafter, a virus inactivation was carried out by means of S/D treatment. In the then following anion exchange chromatography, a VWF containing wash fraction is obtained which is above all contaminated with fibrinogen and fibronectin. By titration to pH 5.2, the protein solution is subjected to a precipitation step where the majority of fibronectin and fibrinogen were removed. Thereafter, ultrafiltration and diafiltration were carried out, the protein solution being concentrated about 7 times and diafiltrated against the running buffer of the following chromatography. The resulting protein solution contained about 930 µg/ml VWF antigen, 270 µg/ml fibrinogen antigen and 2400 µg/ml fibronectin antigen. The protein solution was applied onto a hydroxylapatite column equilibrated in 10 mM Na phosphate, pH 7.0 (CHT type 1, Bio-Rad, Munich, Germany). The flow fraction contained about 560 µg/ml VWF antigen, 5 µg/ml fibrinogen antigen, and 50 µg/ml fibronectin antigen. The mass balance results in a step yield of 78% for the VWF antigen and 73% for the VWF activity.

A protein solution previously purified in this way was titrated to pH 6.0 for another inventive purification. Thereafter, the solution was applied onto a hydroxylapatite column (CHT type 1, Bio-Rad, Munich, Germany), which had been equilibrated in the running buffer (20 mM Na phosphate, pH 6.0). VWF was bound quantitatively. A first elution was carried out with 45% elution buffer B (400 mM Na phosphate, pH 6.0), the second with 100% B. The applied protein solution contained 540 µg/ml VWF antigen, 4 µg/ml fibrinogen and 48 µg/ml fibronectin. The VWF activity in this solution was 46 U/ml. The first elution fraction contained 38 µg/ml VWF antigen, 2 µg/ml fibronectin antigen and had a VWF activity of 0.7 U/ml. The fibrinogen-antigen concentration was below the detection limit of 1 µg/ml. The fraction of interest (2$^{nd}$ elution fraction) had a VWF antigen concentration of 173 µg/ml and a VWF activity of 23 U/ml. Neither fibrinogen antigen nor fibronectin antigen could be detected. The residual activity of factor VIII was also below the detection limit. The specific VWF activities could be raised from 85 U/mg VWF antigen to 133 U/mg VWF antigen. The specific VWF activity value of the first elution fraction of 18 U/mg VWF antigen proves that in particular sparsely active VWF molecules are separated. The yield of VWF activity is 84% and that of VWF antigen is 51%.

TABLE 2

Increase in the specific VWF activity of a previously purified, VWF containing plasma fraction by means of hydroxylapatite chromatography on a laboratory scale

|  | VWF antigen [µg/ml] | VWF activity [U/ml] | Specific VWF activity [U per mg VWF antigen] |
|---|---|---|---|
| Stock material of chromium I | 560 | 46 | 85 |
| Elution 1 Chromium II | 38 | 0.7 | 18 |
| Elution 2 Chromium II | 173 | 23 | 133 |

The WVF antigen concentration was determined by means of the STA® Compact of Diagnostic Stago company (Roche Diagnostics, Mannheim, Germany) and its test reagents (STA LIA vWF).

The VWF activity was determined as ristocetin cofactor activity via platelet agglutination using the BCT® Analyzer (Behring Coagulation Timer, Dade Behring, Schwalbach, Germany). The ristocetin cofactor assay determines the binding capacity of VWF to the platelet receptor glycoprotein Ib/IX under the influence of the ristocetin antibiotic.

EXAMPLE 2

Increase in the Specific VWF Activity of a Previously Purified, VWF Containing Plasma Fraction by Means of Hydroxylapatite Chromatography on a Technical School Scale The starting solution was prepared according to Example 1 up to the first chromatography. The resulting protein solution contained about 1.43 mg/ml VWF antigen at a total protein concentration of 3.79 mg/ml. The specific activity was 36.4 U/mg protein. Columns having a diameter of 10 cm were used for the chromatographic purification. In a first chromatographic purification step, the protein solution was applied onto a hydroxylapatite column equilibrated in 10 mM Na phosphate, pH 7.0 (CHT Type 1, Bio-Rad, Munich, Germany) with 1.0 l gel bed volume. The flow fraction (fraction of interest 1) contained about 0.67 mg/ml VWF antigen at a total protein concentration of 0.86 mg/ml. The specific activity was 68.7 U/mg protein and the specific VWF activity was 96.5 U/mg VWF antigen.

A protein solution previously purified in this way was titrated to pH 6.5 for further purification and for separation of sparsely active VWF molecules. Thereafter, the solution was applied onto a hydroxylapatite column (CHT type 2, Bio-Rad, Munich, Germany) with a gel bed volume of 1.5 l, l which had been equilibrated in the running buffer (20 mM Na phosphate, pH 6.5). VWF was bound quantitatively. In order to separate sparsely active VWF molecules, a first elution was carried out with 220 mM Na phosphate, pH 6.5. Fraction of interest 2 having a protein concentration of 0.20 mg/ml and a VWF antigen content of 0.13 mg/ml was then eluted with 300 mM Na phosphate, pH 6.5. The specific VWF activity of 87.5 U/mg VWF antigen could be raised to 171 U/mg VWF antigen by this chromatographic step. In this connection, the specific activity was raised to 107 U/mg protein. Contaminations such as fibronectin, fibrinogen or factor VIII were below the detection limit.

The change in the specific VWF activities during the purification process (see Table 3) shows that during the first chromatography this parameter is not influenced positively. However, the second chromatographic step according to the invention is excellently suited to increase the specific VWF activity, which corresponds to a separation of sparsely active VWF molecules.

TABLE 3

Increase in the specific VWF activity of a previously purified, VWF containing plasma fraction by means of hydroxylapatite chromatography on a technical school scale

|  | VWF antigen [mg/ml] | Specific activity [U per mg protein] | Specific VWF activity [U per mg VWF antigen] |
|---|---|---|---|
| Stock | 1.43 | 36.4 | 96.5 |
| Fraction of interest 1 | 0.67 | 68.7 | 87.5 |
| Fraction of interest 2 | 0.13 | 107 | 171 |

VWF antigen and VWF activity were determined as defined in Example 1.

The protein was determined according to the Lambert Beer law ($A = \epsilon \cdot c \cdot d$), wherein A=absorption at 280 nm $\epsilon$=coefficient of absorption (here theoretical coefficient of absorption 0.75 cm$^2$/mg)

c=protein concentration in mg/ml d=layer thickness in cm.

EXAMPLE 3

Increase in the Specific VWF Activity of a Previously Purified VWF Containing Plasma Fraction by Means of Binding Fluoroapatite Chromatography The starting solution was prepared in accordance with Example 1 up to the second chromatography. The protein solution contained a specific activity of 64.8 U/mg and a specific VWF activity of 95.1 mg/ml at a protein concentration of 0.83 mg/ml.

The protein solution was titrated to a pH value of 6.0 by the addition of HCl. Thereafter, the solution was applied onto a fluoroapatite column (CFT type 1, Bio-Rad, Munich, Germany) with a gel bed volume of 13.2 ml, which had been equilibrated in the running buffer (20 mM Na phosphate, pH 6.0). Part of VWF was bound. A separation of sparsely active VWF molecules was obtained by a first elution with a buffer containing 241 mM Na phosphate, pH 6.0 (fraction of interest 1). Fraction of interest 2 having a protein concentration of 0.12 mg/ml and a VWF antigen content of 0.06 mg/ml was then eluted with 400 mM Na phosphate, pH 6.0. By this chromatographic step, the specific VWF activity could be raised to 152 U/mg VWF antigen. In this connection, the specific activity was raised to 77 U/mg protein. On account of the weaker binding of VWF under the chosen pH conditions, no complete binding of VWF occurs so that part is in the flow fraction.

TABLE 4

Increase in the specific VWF activity of a previously purified VWF containing plasma fraction by means of fluoroapatite chromatography

| | VWF antigen [mg/ml] | Specific activity [U per mg protein] | Specific VWF activity [U per mg VWF antigen] |
|---|---|---|---|
| Stock | 0.57 | 64.8 | 95.1 |
| Flow | 0.07 | 47.1 | 89 |
| Fraction of interest 1 | 0.06 | 39.3 | 71.7 |
| Fraction of interest 2 | 0.06 | 77 | 152 |

Additional Citations

The following citations are mentioned additionally in connection with various analytical methods.

VWF Activity:

Veyradier A, Fressinaud E, Meyer D (1998): Laboratory diagnosis of von Willebrand disease. Int J Lab Res 28 (4): 201-210.

VWF Antigen:

Budde U, et al. (1984): Acquired von Willebrand's disease in the myeloproliferative syndrome. Blood 64 (5): 981-985.

Newman D J, Henneberry H, Price C P (1992): Particle enhanced light scattering immunoassay. Ann Clin Biochem 29 (Pt1): 22-42.

Fibronectin Antigen:

Sandberg L, et al (1985): Plasma fibronectin levels in acute and recovering malnourished children. Clin Physiol. Biochem. 3(5):257-264.

Colli A, et al. (1986): Diagnostic accuracy of fibronectin in the differential diagnosis of ascites. Cancer: 58(11):2489-2493.

Fibrinogen Antigen:

Ernst E, Resch K L (1993): Fibrinogen as a cardiovascular risk factor: a meta-analysis and review of the literature. Ann Intern Med.: 118(12):956-963.

Jelic-Ivanovic Z, Pevcevic N (1990): Fibrinogen determination by five methods in patients receiving streptokinase therapy. Clin Chem.: 36(4):698-699.

The invention claimed is:

1. A process for separating a von Willebrand factor (VWF) having a high specific VWF activity from a VWF having a low specific VWF activity, said process comprising the steps: (a) binding VWF to a hydroxylapatite column matrix, (b) washing out VWF having a specific VWF activity less than 70 U per mg VWF antigen using a wash buffer containing 100-300 mM phosphate salt and (c) eluting a VWF having a specific VWF activity greater than 120 U per mg VWF antigen using an elution buffer containing 200-500 mM phosphate salt.

2. The process according to claim 1, characterized in that the binding of step (a) is carried out at a pH between 5 and 7.

3. The process according to claim 1, characterized in that the phosphate salt is selected from the group consisting of sodium phosphate and potassium phosphate.

4. The process according to claim 1, wherein the VWF having a specific VWF activity greater than 120 U per mg VWF antigen eluted in step (c) is substantially free from fibrinogen and fibronectin.

5. The process according to claim 1, characterized in that the hydroxylapatite column matrix is a ceramic hydroxylapatite.

6. The process according to claim 5, characterized in that the ceramic hydroxylapatite is type I or type II.

7. The process according to claim 1, characterized in that a previously purified plasma fraction is used as a starting material.

8. The process according to claim 1, characterized in that a further purified cryoprecipitate solution is used as a starting material.

9. The process according to claim 1, characterized in that a cryoprecipitate solution precipitated with aluminum hydroxide is used as a starting material.

10. The process according to claim 1, characterized in that a chromatographically pre-purified cryoprecipitate solution precipitated with aluminum hydroxide is used as a starting material.

11. The process according to claim 1, further comprising the step of carrying out a pH precipitation prior to step (a) to separate fibronectin.

12. The process according to claim 1, characterized in that a protein solution with recombinantly produced VWF is used as a starting material.

13. The process according to claim 1, characterized in that the hydroxylapatite column matrix contains fluoride ions.

14. The process according to claim 1, wherein the wash buffer has a phosphate salt concentration ranging from 200-300 mM and the elution buffer has a phosphate salt concentration ranging from 250-500 mM.

15. The process according to claim 1, wherein the wash buffer has a phosphate salt concentration ranging from 200-270 mM and the elution buffer has phoshphate salt concentration ranging from 300-400 mM.

* * * * *